「United States Patent [19]

Raymond et al.

[11] Patent Number: 5,047,100
[45] Date of Patent: Sep. 10, 1991

[54] CURCUMIN IN THE DETECTION AND WARNING OF CYANIDE ADULTERATED FOOD PRODUCTS

[75] Inventors: Susan Raymond, Palos Hills; Michael J. Greenberg, Northbrook; Firoz Rajani, Wheaton, all of Ill.

[73] Assignee: Northwestern Chemical Co., West Chicago, Ill.

[21] Appl. No.: 382,155

[22] Filed: Jul. 18, 1989

Related U.S. Application Data

[63] Continuation-in-part of Ser. No. 157,918, Feb. 19, 1988.

[51] Int. Cl.$^5$ ............................................. B32B 33/00
[52] U.S. Cl. ..................................... 156/64; 116/206; 229/102; 428/916
[58] Field of Search .......................... 156/64; 229/102; 116/206; 383/5; 428/916; 426/87, 126

[56] References Cited

U.S. PATENT DOCUMENTS

| | | |
|---|---|---|
| 3,312,528 | 4/1967 | McConnaughey . |
| 4,019,860 | 4/1977 | Fischer et al. . |
| 4,163,803 | 8/1979 | Goldscher . |
| 4,215,170 | 7/1980 | Oliva ............................... 156/230 X |
| 4,263,333 | 4/1981 | Maing et al. . |
| 4,307,117 | 12/1981 | Leshik . |
| 4,521,492 | 6/1985 | Allen ................................. 106/20 X |
| 4,543,370 | 9/1985 | Porter et al. . |
| 4,746,616 | 5/1988 | Honigs et al. . |
| 4,756,804 | 7/1988 | Driscoll et al. . |

FOREIGN PATENT DOCUMENTS 2820981 4/1979 Fed. Rep. of Germany .

OTHER PUBLICATIONS

Tonnesen, H. H. et al., Studies on Curcumin and Curcuminoids, VI. Kinetics of Curcumin Degradation in Aqueous Solution, Z Lebensm Unters Forsch (1985), 180:402–404.
Tonnesen, H. H. et al., Studies on Curcumin and Curcuminoids, VIII. Photochemical Stability of Curcumin, Z Lebensm Unters Porsch (1986), 183:116–122.
Marmion, D. M., Handbook of U.S. Colorants for Foods, Drugs and Cosmetics, Wiley-Interscience Publication, John Wiley & Sons.
Tumeric (Curcumin) Information Brochure, International Life Sciences Institute, May 5, 1986.

Primary Examiner—Richard Bueker
Assistant Examiner—James J. Engel, Jr.
Attorney, Agent, or Firm—Willian Brinks Olds Hofer Gilson & Lione

[57] ABSTRACT

Curcumin is employed for the purpose of detecting and warning of the presence of cyanide in a food, drug, or other oral composition. The curcumin is incorporated into a food packaging material. In the presence of cyanide, the curcumin undergoes a color change causing at least a portion of the packaging material to manifest a color change. The color change is sufficient to be detected by an observer, thereby providing a warning of cyanide adulteration of the product.

27 Claims, No Drawings

CURCUMIN IN THE DETECTION AND WARNING OF CYANIDE ADULTERATED FOOD PRODUCTS

This is a Continuation-In-Part Application of copending U.S. patent application Ser. No. 157,918 filed on Feb. 19, 1988.

FIELD OF THE INVENTION

The present invention relates to the detection of cyanide in food, drug or other oral compositions for the purpose of warning consumers of the presence of cyanide prior to consumption of the composition.

BACKGROUND OF THE INVENTION

Cyanide is a readily available poison which is extremely dangerous and often fatal when consumed in relatively small dosages. The presence of cyanide in foods is difficult to detect since it does not possess an easily noticeable odor or color. As a result, a consumer cannot personally detect or be warned of cyanide adulteration which has occurred in a food product.

Packaging devices have been provided which warn a consumer of potential tampering or adulteration of the packaged products. These systems generally involve a physical modification of the package such as the presence of a plastic seal which when broken indicates tampering. However, if the warning signal given by the package is overlooked by the consumer or circumvented by the tamperer such as by injection, the consumer would not detect adulteration.

Curcumin, also known as turmeric yellow, has been used as a food dye on foods having acid to neutral pH values. Curcumin is the main coloring matter in turmeric which is a dried and ground root of curcuma longa, a perennial herb native to China, India and South America. Curcumin has the chemical name 1,7-bis (4-hydroxy-3-methoxy phenyl) -1,6-heptadiene -3,5-dione and the following structure:

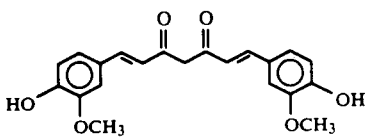

The kinetics of curcumin degradation in aqueous solution was studied by Tannesen and Karlsen in 1985. At pH greater than 7.5, curcumin molecules are extremely unstable with the solution color being an orange red. Below pH 7, curcumin solution is yellow. At pH 7.75, the half life of curcumin is 50 minutes. At pH 10.8, it is about one minute. Degradation products have been identified to be ferulic acid and feruloylmethane.

The photochemical stability was studied by the same scientists and published in 1986. The Curcumin degradation follows first order kinetics with the best stability in methanol (half life being 92.7 hours).

Sodium and potassium cyanide are commercially available and extremely poisonous compounds. When dissolved in water, the resulting aqueous solutions have a high alkalinity. The presence of less than 100 milligrams of sodium or potassium cyanide in food products neutral to sight acid pH will cause the food pH to be alkaline. Accordingly, it is desirable to utilize curcumin to indicate the presence of cyanide in food products.

It is therefore an object of the present invention to employ curcumin to detect and warn of the presence of cyanide in or on food, drug or like products by using curcumin as a cyanide indicator in the product packaging.

SUMMARY OF THE INVENTION

In accordance with one embodiment of the present invention there is provided a method of manufacturing a packaging material which detects and warns of the presence of cyanide in or on a product packaged therein. The packaging material comprises curcumin in an amount sufficient to cause at least a portion of the packaging material to manifest a color change when the curcumin is in the presence of cyanide. The color change is sufficient to be detectable from the original color of the packaging thereby providing a warning of the presence of cyanide.

In accordance with another embodiment of the present invention, there is provided a packaging material which detects and warns of the presence of cyanide in or on a product packaged therein. The packaging material comprises curcumin in an amount sufficient to cause at least a portion of the packaging to manifest a color change when the curcumin is in the presence of cyanide. The color change is sufficient to be detectable from the original color of the packaging thereby providing a warning of the presence of cyanide.

DESCRIPTION OF PRESENTLY PREFERRED EMBODIMENTS

In accordance with the present invention, it has been discovered that curcumin can be incorporated into a packaging material in which a food or oral composition is packaged. Accordingly, when the packaging material is in the presence of cyanide, the packaging, or at least a portion thereof, will manifest a color change sufficient to warn of the presence of cyanide in the food or oral composition. The packaging material may be any known packaging item that is water permeable and transparent to the red-orange color yielded by the curcumin in the presence of cyanide. The packaging material may be flexible wrapping material or may be formed into a box or bottle shape. In any event, curcumin is incorporated in the packaging material in an amount sufficient to display a color change in at least a portion of the packaging material, the color change being detectable and thereby providing a warning of the presence of cyanide in the material contained or packaged therein.

In accordance with one embodiment of the present invention, the curcumin will be incorporated into the packaging material via Transfer Metallisation. The process of Transfer Metallisation is discussed in U.S. Pat. No. 4,215,170. As employed by the present invention, Transfer Metallisation entails applying a thin layer of metallic particles to a transfer agent. The metal may be applied to the transfer agent by various methods as disclosed in U.S. Pat. No. 4,215,170. An adhesive is applied to a substrate, which will eventually be coated with the metallic particles. Alternatively, an adhesive may be applied to the metallised transfer agent. The amount of adhesive, as well as the manner in which it is applied, is as disclosed in U.S. Pat. No. 4,215,170. Prior to the application of the adhesive, however, an amount of curcumin sufficient to cause the color of at least a portion of the packaging to change from its original color to a red-orange color in the presence of cyanide is mixed with the adhesive. In the present invention the substrate will be a food packaging material. Suitable food packaging materials include water permeable paper, cardboard, plastic or any other material capable of being adhesive or varnish coated, as well as being transparent to red-orange light.

Once the curcumin-containing adhesive is applied to the packaging material, the metallised surface of the transfer agent and the adhesive containing side of the packaging material are laminated. Suitable methods of lamination as contemplated by the present invention are disclosed in U.S. Pat. No. 4,215,170. Once the transfer agent and the packaging material have been laminated, the adhesive is cured according to one of the methods disclosed in U.S. Pat. No. 4,215,170. After the adhesive is cured, the transfer agent is peeled away from the packaging substrate, as disclosed in U.S. Pat. No. 4,215,170, leaving behind a metallised packaging material incorporating the curcumin cyanide detector.

The packaging product of the aforesaid method of manufacture will yield a noticeable red-orange staining of the inner portion of the packaging material in the presence of cyanide. As can be discerned from the aforesaid, the packaging manufactured by the aforesaid method incorporates the cyanide detecting curcumin between laminated layers of the packaging material. Hence, for the curcumin to indicate the presence of cyanide, the cyanide must be able to permeate through the packaging material thereby stimulating the curcumin color change. Water is a suitable cyanide carrier. Thus, the requirement that the packaging be water permeable. Furthermore, it is the internal portion of the packaging material which must be examined for the curcumin color change, as the external surface is coated with the metallic particles and, thus, the color change occurring within the packaging may not be noticeable. Accordingly, the red-orange color that the packaging manifests in the presence of cyanide is best viewed from the internal portion of the package wrapping. Therefore, the need for a red-orange light transparent packaging material.

Suitable metals for deposition on the transfer agent include aluminum, copper, silver, nickel, tin, platinum, gold, their alloys and other vaporizable metals. Preferably, however, the present invention contemplates the use of aluminum. The quantity of metal deposited on the transfer agent will be monitored so that the metal particles deposited will form an extremely thin layer. Preferably, the metal particles deposited on the transfer agent should form a layer of about 1000 Angstroms or less. Most preferably, the metal particles deposited on the transfer agent will form a layer of about 50 to about 250 Angstroms thickness.

Appropriate transfer agents have an adherence to the metal particles less than that of the adhesive to be employed. Suitable materials for the transfer agent are untreated polypropylene, polyester, polyethylene, polyvinylchloride, polyamide, co-extrusates and regenerated cellulose, among others. Preferably, however, the transfer agent employed is polypropylene.

The physical form of the curcumin contemplated (i.e., dispersion, dry powder, or solution) by the Transfer Metallisation process is dependent on the particular adhesive system employed. As the physical form of the curcumin must be compatible with the particular adhesive system selected.

The preferred adhesive system of the present invention is an ethylene acrylic acid aqueous emulsion comprising about 30% ethylene acrylic acid and about 70% water available from MORTON INTERNATIONAL, 1275 Lake Avenue, Woodstock, Ill. 60098, or MICHELMAN INC., 9089 Shell Road, Cincinnati, Ohio 45236. When the preferred ethylene acrylic acid adhesive is employed the curcumin is added to the adhesive as a glycerin dispersion containing about 5% by weight curcumin.

The curcumin is mixed with the adhesive so that active curcumin comprises about 0.1% to about 5% by weight of the adhesive. Preferably, however, active curcumin will comprise about 0.5% of the adhesive composition.

The aforesaid curcumin containing adhesive is applied to either metallised the transfer agent or the packaging material substrate in an amount sufficient to cause at least a portion of the packaging to manifest a color change in the presence of cyanide. Preferably, however, the adhesive is applied to the metallised transfer agent.

As already indicated, the present invention contemplates the use of any water permeable, packaging material which is transparent to red-orange light. Preferably, however, the present invention contemplates the use of tissue paper as the packaging material. Preferably, the tissue paper packaging employed in the present invention is at least fifteen pounds per ream tissue paper. Most preferably, the tissue paper packaging contemplated by the present invention is about twenty pounds per ream tissue paper. Where tissue paper is employed as the packaging substrate, the preferred curcumin-containing ethylene acrylic acid adhesive of the present invention is applied to the metallised transfer agent in an amount from about 1.0 to about 2.5 pounds per ream of tissue paper to which the transfer agent is to be laminated. Preferably, however, the curcumin-containing ethylene acrylic acid adhesive is applied to the metallised transfer agent from about 1.5 to about 1.8 pounds per ream of tissue paper to which the transfer agent is to be laminated.

As previously stated, the curcumin of the present invention has a yellowish color in the absence of cyanide. It is preferred that either the packaging material or the adhesive of the present invention contain a whitening agent in an amount sufficient to reduce the noticeability of the curcumin's yellow color without seriously reducing the noticeability of the curcumin's red-orange color in the presence of cyanide. Any suitable whitening agent is contemplated by the present invention. Appropriate whitening agents include, for example, zinc sulfite, calcium carbonate, polymeric whiteners such as ROHM & HAAS OP62, and titanium dioxide to name a few. The preferred whitening agent of the present invention is titanium dioxide. Preferably, the titanium dioxide will comprise from about 1% to about 40% by weight of the packaging material.

Once the mixture of curcumin and the preferred ethylene acrylic acid adhesive is applied to the metallic transfer agent, the aforesaid is subjected to 125° F. heat for a few seconds to drive off water. At which time, the transfer agent and the preferred tissue paper packaging is laminated using a nip roller. The resulting material is then rolled up and stored until ready for application, whereupon, the transfer agent is removed and the resulting curcumin containing packaging material is used as a direct contact food wrapper.

An alternative preferred method contemplates the use of a solvent based varnish in place of the ethylene acrylic acid adhesive composition described above. Preferably, the solvent employed is alcohol. Where a solvent based varnish is employed, preferably the curcumin is dissolved in the varnish so that the curcumin comprises about 0.1% to about 5% by weight of the varnish. Besides solvent and curcumin, the varnish further comprises about 10% to about 20% nitrocellulose. Most preferably, however, the curcumin will comprise about 0.5% by weight of the varnish. The curcumin-containing varnish is then applied to at least a portion of the metallised transfer agent or the packaging material substrate prior to the lamination of the metallised transfer agent and the packaging material.

In another embodiment of the present invention, the curcumin is incorporated into the food packaging by printing on one side of the packaging material with a curcumin ink. The curcumin ink can be prepared as an aqueous emulsion or solution of curcumin in combination with a resin or binder. Aqueous emulsions or organic solvent based inks can be used. Ideally, the ink color will be such so as not to seriously interfere with the red-orange color of the curcumin when in the presence of cyanide. Preferably, the curcumin ink comprises a dispersion of about 10% KALSEC 832104-B, which is a glycerin dispersion of about 5% curcumin available from KALSEC Inc. located in Kalamazoo Mich.; about 88% styrene acrylic aqueous emulsion available from MIDWEST GRAPHIC, 178 Brandon Drive, Glendale Heights, Ill. 60139, under the tradename 5002; and about 2% whitener available from ROHM & HAAS under the tradename OP62.

Any packaging that is water permeable and either transparent to red-orange light or permeable to the red stain created by the curcumin while in the presence of cyanide is contemplated by the present invention. However, the preferred packaging is tissue paper of at least 15 pounds per ream. The most preferred packaging contemplated by the present embodiment is 25 pounds per ream tissue paper which is clay coated on one side and available from JAMES RIVER under the tradename M-1153X.

Any printing method which is suitable for use with the chosen ink is contemplated by the present method as, for example, rotogravure, flexography, offset, or lithography. Preferably, however, the present invention contemplates the use of rotogravure printing.

Once the packaging has been subjected to printing, an adhesive is applied to either the packaging or a backing material, after which the packaging and backing material are laminated. The backing material may be any suitable polymer or paper structure that causes the curcumin to migrate throughout the packaging layers. The backing material may further be selected based on the aesthetic demands of the particular application. The preferred backing material of the present invention is aluminum foil. Most preferably, the aluminum foil will have a thickness of about 0.3 mils.

The lamination of the packaging material and backing material can be carried out using any suitable adhesive. Suitable adhesives include wax, hot melt, casein, polymeric adhesives such as ethylene acrylic acid, or any other adhesive compatible with curcumin and capable of holding the packaging layers together. The adhesive can be applied to either the printed side of the packaging or the surface of the backing material that is to come in contact with the printed side of the packaging. Preferably, however, the adhesive is applied to the printed side of the packaging material. Where tissue paper is the packaging material employed, it is preferred that the adhesive is a molten wax of a paraffin microcrystalline blend. Most preferably, the adhesive will be MULTIWAX 110-X, available from NATIONAL WAX COMPANY, Skokie, Ill., or WITCO CHEMICAL COMPANY, New York, N.Y. Preferably, the aforesaid adhesives will be applied to the printed side of the tissue packaging material in an amount from about 3 to about 5 pounds per ream. Upon the application of the molten wax adhesive to the tissue paper, the preferred aluminum foil backing material is laminated to the tissue by the use of a hot nip roller.

The products of the present invention will yield a noticeable red-orange staining of the inner tissue of the food wrapper when contacted with even small quantities of aqueous cyanide solution. This protects against the injection of cyanide solutions as, for example, through a tamper evident package. The wrapper may also exhibit a color change if water is absorbed by powdered cyanide from the atmosphere or food product.

It is to be understood that the present invention contemplates that the curcumin may be applied as a complete layer, interval strip, or other geometric design such as squares, triangles, dots, etc. Moreover, curcumin may be applied whereby a change in color spells out a particular warning or depicts a recognizable warning design, figure, display, pattern, or picture. Such means for detecting the presence of cyanide in the food or oral composition are preferably present to warn the consumer against consumption of the composition when the color change occurs. Additional means for warning the consumer, while not necessary, may be provided. Such means may include a warning message or pictorial warning on the package or nearby display indicating the significance or relevance of the color change with regard to the presence of cyanide.

The following examples are merely intended to illustrate the present invention. It is to be understood that these examples are not to be construed as a limitation of the present invention, the scope of which is defined in the appended claims.

EXAMPLES

EXAMPLE 1

Wrapping materials were manufactured according to the most preferred methods and materials as discussed above. Specifically, 20 pounds per ream tissue paper obtained from JAMES RIVER, Detroit, comprising about 5% titanium dioxide was employed as the substrate. To the tissue paper 1.7 pounds per ream of adhesive was applied, the adhesive comprising about 10% KALSEC 832104-B (available from KALSEC INC.) and about 90% ethylene acrylic acid aqueous emulsion (available from MORTON INTERNATIONAL or MICHELMAN INC.) Upon a polypropylene transfer agent, about a 150 Angstrom thick aluminum film was applied by vacuum deposition as disclosed in U.S. Pat. No. 4,215,170. The transfer agent and the tissue paper substrate were then laminated together using a nip roller and then heat cured. Whereupon, after a period of approximately about two days the two materials were separated.

The material was used to wrap chewing gum sticks which were further wrapped in a conventional outer package. A 25% aqueous solution of potassium cyanide was prepared and 120 microliters were injected into the middle of the package. Within five minutes the package was opened and the metallised wrappers exhibited an orange-red stain which increased with intensity over a two week period.

A control package identical to the one discussed above was prepared, except for the presence of curcumin, and treated as above. The gum and packaging appeared wet, but otherwise looked normal.

EXAMPLE 2

A wrapping material was manufactured according to the following method: A clay coated, 25 pound per ream tissue paper was employed. On the uncoated side of the tissue paper was printed by rotogravure a dispersion of 10% KALSEC 832104-B, 88% Styrene Acrylic Emulsion (MIDWEST GRAPHIC 5002), and 2% OP62. The above tissue was laminated to 0.3 mils. thick aluminum foil using 3–5 pounds per ream of MULTIWAX 110-X, (available from NATIONAL WAX COMPANY or WITCO CHEMICAL COMPANY). The aforesaid lamination was accomplished using a hot nip roller.

The above material was used to wrap chewing gum sticks which were further wrapped in a conventional outer packaging. A 25% aqueous solution of potassium cyanide was prepared and 120 microliters were injected into the package. Within five minutes the package was opened and a slight red-orange stain was observed which increased in intensity over a two week period.

A control package which was prepared in the manner as described above, except for the presence of curcumin, and treated in the identical manner as described above. The gum and wrapper were wet, but otherwise appeared normal.

We claim:

1. A method of incorporating a curcumin based cyanide detection system into metallised food packaging comprising the steps of:
   providing a transfer agent;
   providing a water permeable food packaging material transparent to red-orange light;
   depositing on the transfer agent a film of metal particles;
   providing an adhesive;
   mixing with the adhesive an amount of curcumin sufficient to cause at least a portion of the packaging material to manifest a change from its original color to a red-orange color when the curcumin is in the presence of cyanide;
   laminating the packaging material and the metallised transfer agent together with the adhesive disposed between, the lamination being performed before the adhesive is cured so that the metal particles are embedded in the adhesive;
   curing the adhesive; and
   separating the transfer agent from the packaging material, whereupon the packaging material is provided with a film containing curcumin and metallic particles whereby at least a portion of the packaging material manifests a color change in the presence of cyanide.

2. The method of claim 1 wherein the metal is aluminum.

3. The method of claim 1 wherein the film of metal particles is about 1000 Angstroms or less.

4. The method of claim 1 wherein the film of metal particles is about 50 to about 250 Angstroms.

5. The method of claim 1 wherein the transfer agent is polypropylene film.

6. The method of claim 1 wherein the adhesive is an ethylene acrylic acid aqueous emulsion comprising about 30% by weight ethylene acrylic acid and about 70% by weight water.

7. The method of claim 1 wherein curcumin is mixed with the adhesive so that the adhesive comprises about 0.1% to about 5% by weight curcumin.

8. The method of claim 1 wherein curcumin is mixed with the adhesive so that the adhesive comprises about 0.5% by weight curcumin.

9. The method of claim 6 wherein a glycerin dispersion containing about 5% by weight curcumin is mixed with the adhesive.

10. The method of claim 1 wherein the packaging is at least fifteen pounds per ream tissue paper.

11. The method of claim 1 wherein the packaging is about twenty pounds per ream tissue paper.

12. The method of claim 10 wherein the adhesive is applied to the metallised transfer agent in an amount of about 1.0 to about 2.5 pounds per ream of tissue paper to which the transfer agent is to be laminated.

13. The method of claim 10 wherein the adhesive is applied to the metallised transfer agent in an amount of about 1.5 to about 1.8 pounds per ream of tissue paper to which the transfer agent is to be laminated.

14. The method of claim 1 wherein the packaging contains a whitening agent comprising an amount of Titanium Dioxide sufficient to reduce the noticeability of the curcumin's yellow color without seriously reducing the noticeability of the red-orange color of the curcumin when in the presence of cyanide.

15. A method of incorporating a curcumin based cyanide detection system into a metallised food packaging material comprising the steps of:
   depositing on a transfer agent a film of metal particles;
   providing a solvent based varnish;
   providing a water permeable packaging material transparent to red-orange light;
   mixing an amount of curcumin with the solvent based varnish sufficient to cause at least a portion of the packaging material to manifest a color change from its original color to a red-orange color in the presence of cyanide;
   laminating the packaging and the transfer agent together with the varnish disposed between, the lamination being performed before the varnish is cured so that the metal particles are embedded in the varnish;
   curing the varnish;
   separating the transfer agent from the packaging material, whereupon the packaging material is provided with a film containing curcumin and metallic particles whereby at least a portion of the packaging manifests a color change in the presence of cyanide.

16. The method of claim 15 wherein the curcumin is mixed with the varnish so that the varnish comprises about 0.1% to about 5% by weight curcumin.

17. The method of claim 16 wherein the curcumin is mixed with the varnish so that the varnish comprises about 0.5% by weight curcumin.

18. A method for incorporating a curcumin based cyanide detection system into a food packaging material comprising the steps of:
   providing a water permeable packaging material transparent to red-orange light;
   providing a backing material;

providing an ink containing an amount of curcumin sufficient to cause at least a portion of the packaging material to manifest a color change in the presence of cyanide;

printing on one side of the packaging material using the ink;

laminating the packaging material and the backing material together whereupon the packaging material has incorporated an amount of curcumin sufficient to cause at least a portion of the packaging material to manifest a color change in the presence of cyanide.

19. The method of claim 18 wherein the packaging material is tissue of at least 15 pounds per ream.

20. The method of claim 18 wherein the packaging is a 25 pound per ream tissue which is clay coated on one side.

21. The method of claim 18 wherein the ink comprises about 0.1% to about 5% by weight curcumin.

22. The method of claim 18 wherein the ink comprises about 0.5% by weight curcumin.

23. The method of claim 18 wherein the ink is printed on the packaging by rotogravure.

24. The method of claim 18 wherein the backing material is aluminum foil.

25. The method of claim 24 wherein the aluminum foil has a thickness of about 0.3 mil.

26. The method of claim 20 wherein the adhesive is wax applied to the printed side of the tissue.

27. The method of claim 20 wherein the adhesive is a molten wax of a paraffin microcrystalline blend applied to the printed side of the tissue from about 3 to about 5 pounds adhesive per ream of tissue.

* * * * *